US007045491B2

(12) United States Patent
Hourigan

(10) Patent No.: US 7,045,491 B2
(45) Date of Patent: May 16, 2006

(54) BAR SOAP COMPOSITION WITH REDUCED BAR WEAR PROPERTIES

(75) Inventor: Regina Hourigan, Metuchen, NJ (US)

(73) Assignee: Colgate-Palmolive Company, New York, NY (US)

( * ) Notice: Subject to any disclaimer, the term of this patent is extended or adjusted under 35 U.S.C. 154(b) by 24 days.

(21) Appl. No.: 10/970,036

(22) Filed: Oct. 21, 2004

(65) Prior Publication Data

US 2005/0107273 A1 May 19, 2005

Related U.S. Application Data

(60) Provisional application No. 60/514,992, filed on Oct. 28, 2003.

(51) Int. Cl.
*A61K 7/50* (2006.01)

(52) U.S. Cl. ...................... 510/141; 510/152; 510/155; 510/156; 510/481; 510/484; 510/499; 510/505

(58) Field of Classification Search ................ 510/141, 510/155, 156, 481, 499, 505
See application file for complete search history.

(56) References Cited

U.S. PATENT DOCUMENTS

| | | | |
|---|---|---|---|
| 2,438,091 | A | 3/1948 | Lynch |
| 2,528,378 | A | 10/1950 | Mannheimer |
| 2,658,072 | A | 11/1953 | Kosmin |
| 4,303,543 | A | 12/1981 | Mansy |
| 5,286,755 | A | 2/1994 | Kauffmann et al. |
| 5,340,492 | A | 8/1994 | Kacher et al. |
| 6,310,015 | B1 | 10/2001 | Diez et al. |
| 6,403,543 | B1 | 6/2002 | George |
| 6,514,919 | B1 | 2/2003 | Lambino et al. |
| 2003/0166480 | A1 | 9/2003 | Sachdev |

FOREIGN PATENT DOCUMENTS

| | | | |
|---|---|---|---|
| EP | 0 291 334 | A2 | 11/1988 |
| EP | 1 156 101 | A | 11/2001 |

OTHER PUBLICATIONS

International Search Report for corresponding International Application No. PCT/US2004/036008 (mailed Apr. 3, 2005).
Patent Abstracts of Japan, vol. 1995, No. 5, Jun. 30, 1995 & JP 07 034100 A (Kao Corp.) Feb. 3, 1995 (abstract).
CTFA Int'l Cosm. Ingred. Dict., 4th Ed., J. Nikitakis, G. McEwan, Jr., & J. Wenninger (eds), The CTFA, Washington, DC (1991) pp. 509-514.
Conditionaing Agents for Hair & Skin, Schueller & Romanowski (eds.), Marcel Dekker, Inc. NY, 1999, pp. 201-221.

*Primary Examiner*—Necholus Ogden
(74) *Attorney, Agent, or Firm*—Kristyne A. Bullock

(57) ABSTRACT

A non-clear (translucent to opaque) cleansing bar comprising: (a) from about 3 to about 40 weight % anionic soap; (b) from about 4 to about 40 weight % of at least one synthetic surfactant; (c) from 0.1 to about 10 weight % of a gelling agent from the group consisting of dibenzylidene sorbitol, dibenzylidene xylitol, dibenzylidene ribitol, and mixtures thereof; (d) from about 5 to about 60 weight % of a humectant provided that glycerin is a component of the humectant and is present in an amount of about 2 to about 10 weight %; and (e) water; wherein all amounts are in % by weight based on the weight of the entire composition.

31 Claims, No Drawings

BAR SOAP COMPOSITION WITH REDUCED BAR WEAR PROPERTIES

FIELD OF THE INVENTION

This invention relates to cleansing bar compositions which are translucent, pearlized, or opaque; have good structural integrity; exhibit good cleansing properties; and provide effective and mild cleansing, pleasing aesthetics, and a low wear rate. This case is related to U.S. Provisional Application No. 60/514,992, filed Oct. 28, 2003.

BACKGROUND OF THE INVENTION

Bar soaps are still widely used. With regard to cost and aesthetics, wear rate (also called use up rate) is an important property. Consumer perceived economy of bar soaps is determined by the amount of mush (also called slough) that occurs as the bar surface hydrates. The mush is considered undesirable by consumers since it is easily removed and washed off of the bar surface, leaving the user with less usable soap. Bar use up rate is another indication of the economy of the bar soap. Use up is determined by the physical abrasion (mechanical action) on the bar and is related to bar hardness and shape.

In addition to the economy of a bar, there is also a desire to maintain good foaming and cleaning abilities. The quality and quantity of lather produced by washing with a bar is associated with the cleansing ability of the bar. Other qualities desired are good rinsability, mildness to the skin, and delivery of fragrance to the user's skin. The combination of an efficient bar soap with effective cleansing and bar aesthetics has been often attempted.

U.S. Patent Application Publication Number 2003/0166480 describes certain ranges and combination of soap, synthetic surfactant, water, lower monohydric alcohol, humectant, structurant and gellant which can be used to bring about an excellent combination of desirable characteristics of a translucent or transparent bar composition.

U.S. Pat. No. 6,514,919 discloses a clear cleansing bar that does not form gel or mush, does not crack upon drying, and is non-irritating to the eyes. The clear bar composition in this reference contains dibenzylidene sorbitol ("DBS") as the gelling agent. This reference does not, however, address non-clear cleansing bars composed of sodium soaps and is silent to the combination of glycerin and DBS.

U.S. Pat. No. 5,340,492, describes cleansing bars with a rigid interlocking mesh of neutralized carboxylic acids. The bars are cleansing bars with excellent smear properties.

U.S. Pat. No. 6,403,543, describes the suspension of particles in a bar soap. This suspension is achieved by using a gel matrix in which particles are suspended before addition to the soap mixture.

U.S. Pat. No. 6,310,015 describes a translucent/transparent/moisturizing cleansing bar.

It has now been found that a combination of DBS and glycerin gives an especially good product, especially as it relates to forming a soap bar which is not clear, and exhibits a longer life as compared to a DBS only bar. The richness of the aesthetics of the non-clear bar can also be enhanced by the inclusion of encapsulated fats/oils or emollient esters the form of beads.

SUMMARY OF THE INVENTION

In accordance with the composition, there is provided a non-clear (also referred to as a non-transparent or translucent to opaque) cleansing bar comprising:

(a) from about 3 to about 40 weight % anionic soap; (b) from about 4 to about 40 weight % of at least one synthetic surfactant; (c) from 0.1 to about 10 weight % of a gelling agent from the group consisting of dibenzylidene sorbitol, dibenzylidene xylitol, dibenzylidene ribitol, and mixtures thereof; (d) from about 5 to about 60 weight % of a humectant provided that glycerin is a component of the humectant and is present in an amount of about 2 to about 10 weight %; and (e) water (particularly in a range of 14–45 weight % and more particularly as a minimum of about 17 weight % and a maximum of about 20, 25, 30, or 35 weight % of the bar composition); wherein all amounts are in % by weight based on the weight of the entire composition.

Additionally other optional ingredients may be included such as one or more members selected from the group consisting of:

(f) from 0 to about 5 wt. % of one or more secondary structurants selected from the group consisting of (i) cellulose and guar derivatives, including but not limited to hydroxypropyl cellulose; (ii) acrylic acid polymers; (iii) polyacrylamides; (iv) alkylene/alkylene oxide polymers; (v) clays such as smectite hydrophilic and/or organo clays; (vi) hydrated and fumed silicas (vii) gelatin; (ix) xanthan and guar gums; (x) carrageenan; (xi) agar; and (xii) alginates; and (g) 0.2–3 weight % of a monohydric alcohol such as 0.1–2 weight % of an alcohol selected from the group consisting of methanol, ethanol, propanol and isopropanol, especially ethanol.

DETAILED DESCRIPTION OF THE INVENTION

The anionic soap that is used is a long chain alkyl (C12–18) with some unsaturation possible, and may have up to 20% of bonds as a carboxylic acid salt (sodium, potassium, ammonium or hydroxyethyl ammonium cations). While the overall amount of the soap is in the range of 3–40%, more particular ranges include a minimum of about 5 or 10 weight % of the composition, and a maximum of about 25, 30, or weight % of the composition. Thus, one particular range may be from 5–30 weight %, with other particular ranges being from 5–25 weight %, 10–30 weight % and 10–25 weight %.

The synthetic surfactants useful in this invention include anionic, amphoteric, nonionic, zwitterionic, and cationic surfactants. Examples of anionic surfactants include but are not limited to soaps, alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and the like. Alkyl chains for these surfactants are C8–22, preferably C10–18 and, more preferably, C12–14 alkyls. Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols (C8–18 carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, for example, carboxy, sulfonate, sulfate, phosphate, or phosphonate. A general formula for these compounds is:

$$\begin{array}{c}(R^3)_x\\ |\\ R^2—Y^{(+)}—CH_2—R^4—Z^{(-)}\end{array}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups. Examples include: 4-[N,N-di(2-hydroxyethyl)-N-octadecylammonio]-but-ane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio)propane- 1-sulfonate; 3-(N,N-dimethyl-N-hexadecylammonio)-2-hydroxypropane-1-sulfonate; 4-(N,N-di(2-hydroxyethyl)-N-(2 hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate; N-alkyltaurines, such as the one prepared by reacting dodecylamine with sodium isethionate according to the teaching of U.S. Pat. No. 2,658,072; N-higher alkyl aspartic acids, such as those produced according to the teaching of U.S. Pat. No. 2,438,091; and the products sold under the trade name "Miranol" and described in U.S. Pat. No. 2,528,378. Other amphoterics such as betaines are also useful in the present composition. Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

A variety of cationic surfactants known to the art may also be used in this invention. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Other cationic surfactants which may be used are disclosed in U.S. Pat. No. 4,303,543 (for example, see column 4, lines 58 and column 5, lines 1–42, incorporated herein by reference as to the listing of these cationic surfactants. Also see CTFA *Cosmetic Ingredient Dictionary,* 4th Edition 1991, pages 509–514 for various long chain alkyl cationic surfactants; incorporated herein by reference as to the listing of cationic surfactants.

Nonionic surfactants useful in this invention can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

(a) Polyethylene oxide condensates of alkyl phenols, for example, the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

(b) Products formed from the condensation of ethylene oxide with the product resulting from the reaction of propylene oxide and ethylene diamine products which may be varied in composition depending upon the balance between the hydrophobic and hydrophilic elements ("HLB" value) which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory. One particular group of products are those having an HLB values sufficient to cleanse and provide an acceptable level of foam.

(c) Condensation products of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (for example, Tween 20-polyoxyethylene (20) sorbitan monolaurate).

(d) Long chain tertiary amine oxides corresponding to the following general formula:

$$(R^{11})(R^{12})(R^{13})N \rightarrow O$$

wherein $R^{11}$ contains an alkyl, alkenyl or monohydroxy alkyl radical of from about 8 to about 18 carbon atoms, from 0 to about 10 ethylene oxide moieties, and from 0 to 1 glyceryl moiety, and, $R^{12}$ and $R^{13}$ may be the same or different and each contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyidodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3- -hydroxypropyl)amine oxide, dimethylhexadecylamine oxide.

(e) Long chain tertiary phosphine oxides corresponding to the following general formula:

$$(R^{21})(R^{22})(R^{23})P \rightarrow O$$

wherein $R^{21}$ contains an alkyl, alkenyl or monohydroxyalkyl radical ranging from 8 to 20 carbon atoms in chain length, from 0 to about 10 ethylene oxide moieties and from 0 to 1 glyceryl moiety and $R^{22}$ and $R^{23}$ are each alkyl or monohydroxyalkyl groups containing from 1 to 3 carbon atoms. The arrow in the formula is a conventional representation of a semipolar bond. Examples of suitable phosphine oxides are: dodecyidimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl)phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyidi(2-hydroxyethyl)phosphine oxide, tetradecylmethyl-2-hydroxypropylphosphine oxide, oleyidimethylphosphine oxide, 2-hydroxydodecyldimethylphosphine oxide.

(f) Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide, and (g) Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

The primary structurant of the bar composition is a gellant selected from the group consisting of dibenzylidene sorbitol, dibenzylidene xylitol, dibenzylidene ribitol, and mixtures thereof. Particular amounts of such primary gellants include quantities of the gellant can include a minimum of at least 0.1 or 0.5 weight % and a maximum of 1 or 2 weight %, with particular ranges being 0.1–2 weight % and 0.5–2 weight %. A preferred range of the dibenzylidene sorbitol gellant is about 0.2% to about 1.0%.

A secondary structurant (a material that makes the bar harder) can also optionally be included in the composition. Exemplary of a structurant is alkali halides and alkali metal sulfates such as sodium chloride and sodium sulfate. Particular levels of such a secondary structurant are a minimum of about 0.1 or 0.2 weight % and a maximum of 1, 2, 3 or 4 weight %. Examples of particular ranges include 0.1–4 weight %, 0.1–2 weight %, and 0.2–4 weight %. It is preferable that the secondary structurant be at least about 1% and be selected to be sodium chloride.

A humectant is a polyhydric alcohol organic material which assists in solubilizing soap. Examples of such materials include propylene glycol, dipropylene glycol, glycerin, sorbitol, mannitol, xylitol, hexylene glycol, and the like. More particular values for humectants include a minimum of about 8, 10, 15 or 20 weight %, and a maximum off about 50, 40, or 30 wt. % of the composition. A particular feature of this humectants ingredient is the requirement that the humectant must include glycerin in an amount of at least about 2 weight % of the bar and a maximum of about 10 weight %. Thus, particular ranges for humectants include 8–50 weight %, 10–50 weight %, 15–50 weight %, 10–40 weight %, 15–50 weight %, and 20–50 weight %. The preferred amount of glycerin in the bar product is from about 2.0 to about 6.0 weight %.

Water present in the bar composition may be selected to be a particular minimum of about 17 weight % and a maximum of about 20, 25, 30, or 35 weight % of the bar composition.

Lower monohydric alkanols may also be present in the composition. Examples of suitable lower monohydric alkanols are methanol, ethanol, propanol, isopropanol, and the like. More particular values for the quantity of lower monohydric alkanol present in the composition are a minimum of 0.1 or 0.2 weight % and a maximum quantity is about 1 or 2 weight %. Thus, particular ranges include 0.1–2 weight % and 0.2–2 weight %.

Optional ingredients which can be present in the composition include skin conditioning agents (excluding the humectants listed above), fragrance, dyes, chelating agents such as EDTA, antimicrobial materials such as triclocarban, triclosan and the like, preservatives such as hydantoins, imidazolines and the like. The fragrance can be absent or be present at about 0.001 to about 2 wt. % of the composition.

Skin conditioning ingredients (including emollients) may also be included in the compositions of the invention. Such ingredients include:

(a) various fats and oils (examples include soybean oil, sunflower oil, canola oil, various unsaturated long chain oils and fats in general, shea butter and the like. Quantities of these fats and oils can be a minimum that provides a skin feel up to a maximum that provides skin feel while still achieving translucency and wear rate of the composition. Generally, this is about 0.5 to about 4 weight % of the composition preferably about 1.0 to about 3.0 weight %;

(b) glyceryl esters comprising a subgroup of esters which are primarily fatty acid monoglycerides, diglycerides or triglycerides modified by reaction with other alcohols and the like; particularly fatty acids having a carbon chain of 12 to 18 carbons (for example, PEG 6 caprylic/capric triglycerides, PEG 80 glyceryl cocoate, PEG 40 glyceryl cocoate, PEG 35 soy glyceride);

(c) alkyloxylated derivatives of dimethicone (for example, such as PEG/PPG-22/24 Dimethicone and PEG-8 Dimethicone);

(d) silicone esters such as those selected from the group consisting of silicon phosphate esters, materials prepared by the esterification reaction of a dimethiconol and a fatty acid (for example, C12–18 fatty acid), and materials prepared by the reaction of a dimethicone copolyol with a fatty acid (for example, Dimethicone PEG-7 isostearate, the partial ester of PEG-7 dimethicone and isostearic acid) (see also: *Conditioning Agents for Hair and Skin*. Edited by R. Schueller and P. Romanowsi, pages 201–221.);

(e) silicone quaternium compounds (such as Silicone Quaternium-8);

(f) lanolin quaternium compounds;

(g) cationic polymers (such as Polyquaternium-6 and Polyquaternium-7); and (h) silicone polymers of the following classes: dimethiconol, dimethicone copolyol, alkyl dimethicone copolyol, dimethicone copolyol amine (see also *Conditioning Agents for Hair and Skin*. Edited by R. Schueller and P. Romanowsi. Pages 201–221).

These skin feel materials can be used in relatively minor quantities that are from about 0.05 to about 3 to 4 weight % of each of these as long as skin feel, wear rate, and translucency are maintained. Mixtures of conditioning agents can also be used.

More particular examples of skin feel conditioning agents that maintain translucency and provide a nice skin feel when added to a translucent composition of the invention at a level of 2 weight % are those selected from the group consisting of: soybean oil, PEG 6 caprylic/capric triglycerides, PEG 80 glyceryl cocoate, PEG 40 glyceryl cocoate, PEG 35 soy glycerides, caprylic/capric triglycerides, PEG 8, dimethicone, PEG/PPG-22/24 dimethicone, silicone quaternium-8, dimethicone PEG-7 isostearate, petrolatum, lanolin quat (quaternium-33), capric/caprylic triglycerides, PEG-7 glyceryl cocoate, and mixtures of the foregoing.

The pearlescent compositions of this invention contains may comprise mica at about 0.1 to 1 weight %.

The opaque composition of this invention contains an opacifying agent, such as titanium dioxide, at about 0.1 to 1 wt %.

The bar compositions of this invention may be made in a variety of ways. The translucent, pearlized/pearlescent, or opaque compositions may be prepared according to standard procedures know in the art by pressing (molding) or pouring (cast) methodologies, i.e., placing a liquid into a mold. A preferred procedure is to mix and heat the water and humectants, including glycerin, to 80 degrees C. to 110 degrees C. Once at temperature, the mixture is charged with the gellant and mixing is continued until the batch is clear. At this time a secondary structurant (for example, see U.S. Pat. No. 6,514,919 under the term "synergists") would also be added if utilized. Once the structurant(s) are dissolved, the surfactants are mixed in until uniform. At a temperature of less than 90 degrees C., the optional ingredients are incorporated. The molten soap is then poured into a mold and allowed to cool to a solid form.

Sample formulations of the invention include the following. All quantities, unless otherwise noted, are in weight percent based on the entire composition.

| Ingredient (wt %) | Formula A | Formula B | Formula C |
|---|---|---|---|
| Propylene Glycol | 15.00 | 18.00 | 14.00 |
| Dipropylene Glycol | 3.00 | 0.00 | 4.00 |
| Glycerin | 5.00 | 8.00 | 8.00 |
| Dibenzylidene sorbitol | 0.50 | 0.25 | 0.25 |
| Cocoamidopropyl Betaine (30%) | 9.00 | 10.00 | 10.00 |
| Sodium Chloride | 2.00 | 1.00 | 2.00 |
| Stearic Acid | 13.00 | 9.00 | 16.00 |
| Myristic Acid | 9.00 | 8.00 | 4.00 |
| Coconut Acid | 4.00 | 2.00 | 0.00 |
| Sodium Hydroxide (50%) | 9.37 | 6.86 | 6.82 |
| Ethanol | 1.20 | 0.40 | 1.00 |
| Sucrose | 4.00 | 5.00 | 5.00 |
| Sodium Laureth Sulfate (70%) | 8.00 | 15.00 | 10.00 |
| Cocamide MEA | 3.00 | 1.00 | 2.00 |
| Disodium Lauryl Sulfosuccinate | 4.00 | 5.00 | 6.00 |
| Sodium Lauryl Sulfate | 6.00 | 0.00 | 4.00 |
| Fragrance | 1.00 | 1.00 | 1.00 |
| Water | 1.9299 | 8.4899 | 4.9299 |
| Soybean Oil | 1.00 | 1.00 | 1.00 |
| Colorant | 0.0001 | 0.0001 | 0.0001 |
| Total | 100 | 100 | 100 |

| Ingredient (wt %) | Formula D | Formula E | Formula F |
|---|---|---|---|
| Propylene Glycol | 22.00 | 13.00 | 12.00 |
| Dipropylene Glycol | 0.00 | 6.00 | 0.00 |
| Glycerin | 6.00 | 6.00 | 7.00 |
| Dibenzylidene sorbitol | 0.75 | 0.25 | 0.50 |
| Cocoamidopropyl Betaine (30%) | 6.00 | 10.00 | 7.00 |
| Sodium Chloride | 0.00 | 1.00 | 2.00 |
| Stearic Acid | 17.00 | 10.00 | 16.00 |
| Myristic Acid | 6.00 | 8.00 | 8.00 |
| Coconut Acid | 5.00 | 4.00 | 5.00 |
| Sodium Hydroxide (50%) | 9.94 | 8.00 | 10.38 |
| Ethanol | 1.00 | 0.50 | 1.00 |
| Sucrose | 2.00 | 2.00 | 3.00 |
| Sodium Laureth Sulfate (70%) | 15.00 | 16.00 | 15.00 |
| Cocamide MEA | 0.00 | 2.00 | 0.00 |
| Disodium Lauryl Sulfosuccinate | 2.00 | 3.00 | 2.50 |
| Sodium Lauryl Sulfate | 2.00 | 3.00 | 3.00 |
| Fragrance | 1.00 | 1.00 | 1.00 |
| Water | 2.3099 | 4.2499 | 4.6199 |
| Soybean Oil | 2.00 | 2.00 | 2.00 |
| Colorant | 0.0001 | 0.0001 | 0.0001 |
| Total | 100 | 100 | 100 |

In a special embodiment of this invention, translucent bars can be made with beads of encapsulated fats/oils or emollient esters.

The range of water can be altered as the level of surfactants, soap, or humectants are altered. In order to maintain bar hardness and clarity the ratio of the soaps used is important. The soap is usually comprised of the soluble salts of stearate, myristate, and cocoate. By altering the ratio of the longer chained stearate to the shorter chained myristate one can create a hard, translucent bar soap. For such hard, translucent soaps particular ratios of stearate:myristate are 1.5 to 3.5:1, preferably about 1.6 to 2.25:1. The levels of humectants can also be altered, the range of dipropylene glycol is from 0 to 6 weight % and the range of propylene glycol is 14 to 22%. The surfactant levels can be manipulated to alter the lather profile where sodium laureth sulfate can vary from 10 to 14 weight %, disodium lauryl sulfosuccinate can vary from 2 to 6 weight %, sodium lauryl sulfate can vary from 2 to 6 weight % and cocamide monoethanolamide ("CMEA") can vary from 0 to 3 weight %. Soybean oil in the formula examples above serves as a placeholder for emollients/skin conditioning materials. All of these can be used to produce translucent bars.

One particular embodiment is a translucent, pearlized, or opaque composition comprising (a) about 3 to about 40 wt. % soap, (b) about 4 to about 40 wt. % of at least one synthetic surfactant, (c) about 14 to about 45 wt. % water, (d) from 0 to about 3 wt. % lower monohydric alcohol, (e) about 5 to about 60 wt. % of a humectant where about 2 to 10 wt % is glycerin, (f) from 0 to about 5 wt. % of a structurant, (g) from 0.1 to about 1.5 wt. % of dibenzylidene sorbitol as a gelling agent.

The compositions according to the present invention is useful in reducing the bar wear rate while having excellent cleansing and foaming properties.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C. unless otherwise indicated. The amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., 7$^{th}$ ed. 1997).

Examples 1–2 and Comparatives 1–2

Each of the exemplified compositions can be prepared in a similar manner by combining the ingredients in a heated vessel. A bar can be made with the types and amounts of ingredients listed in Table A, using the following method. Mix and heat the water, cocoamidopropyl betaine, and humectants, including glycerin, to 80 degrees C. to 110 degrees C. Once at temperature, the mixture is charged with the gellant and mixing is continued until the batch is clear. Once the gellant is fully dissolved, the sodium chloride is added. Once the sodium chloride is dissolved, the remaining surfactants are mixed in until uniform. Following the surfactants, if desired, stearyl alcohol, a structurant, is added and mixed until clear. At a temperature of less than 90 degrees C., the optional ingredients are incorporated. The molten soap is then poured into a mold and allowed to cool to a solid form.

The samples made according to the formula described in TABLE A were tested for bar wear and the results are also listed in TABLE A. The test bars were washed under controlled time and temperature for a total of 9 washes. Each wash lasted 30 seconds. Bar weight was taken before the test and after a 24 hour drying period (from the time of the last wash). Because the use up rate is proportional to the bar surface area, consistent shapes were used when making comparisons.

TABLE A

| | Bar Products | | | |
|---|---|---|---|---|
| Ingredient (wt %) | Example 1 (wt %) | Comparative 1 (wt %) | Example 2 (wt %) | Comparative 2 (wt %) |
| Propylene Glycol | 16.00 | 16.00 | 16.00 | 16.00 |
| Dipropylene Glycol | 2.00 | 6.00 | 2.00 | 6.00 |
| Glycerin | 4.00 | — | 4.00 | — |
| Dibenzylidene sorbitol | 0.25 | 0.25 | 0.25 | 0.25 |
| Cocoamidopropyl Betaine (30% active) | 8.73 | 7.00 | 8.73 | 7.00 |
| Sodium Chloride | 1.00 | 1.00 | 1.00 | 1.00 |
| Stearic Acid | 12.00 | 12.00 | 9.23 | 9.23 |
| Myristic Acid | 7.30 | 7.30 | 7.30 | 7.30 |
| Coconut Acid | 3.50 | 3.50 | 3.50 | 3.50 |
| Sodium Hydroxide (50% active) | 6.77 | 6.77 | 5.86 | 5.86 |
| Ethanol | 0.20 | 0.20 | 0.20 | 0.20 |
| Sucrose | 4.00 | 4.00 | 4.00 | 4.00 |
| Sodium Laureth Sulfate (70% active) | 12.00 | 12.00 | 12.00 | 12.00 |
| Cocamide MEA | 2.00 | 1.00 | 2.00 | 1.00 |
| Disodium Lauryl Sulfosuccinate | 4.50 | 4.50 | 4.50 | 4.50 |
| Sodium Lauryl Sulfate | 4.00 | 4.00 | 4.00 | 4.00 |
| Stearyl Alcohol | 3.00 | 3.00 | 3.00 | 3.00 |
| Fragrance | 1.00 | 1.00 | 1.00 | 1.00 |
| Water | 5.2499 | 7.9799 | 8.9299 | 11.6599 |
| Soybean Oil | 2.50 | 2.50 | 2.50 | 2.50 |
| Colorant | 0.0001 | 0.0001 | 0.0001 | 0.0001 |
| Total | 100 | 100 | 100 | 100 |
| % Bar Wear | 9.4 +/− 0.5 | 12.3 +/− 0.5 | 12.3 +/− 0.5 | 15.7 +/− 0.5 |

Comparatives 1 and 2 are bars made as described in Examples 1 and 2, using the dibenzylidene sorbitol as a gellant, but without glycerin. A second difference in the Comparatives from the Examples is the surfactant system. Differences are as follows.

TABLE B

| EXAMPLES | COMPARATIVES |
|---|---|
| Cocoamidopropyl Betaine 8.73% | Cocoamidopropyl Betaine 7.00% |
| Cocamide MEA 2.00% | Cocamide MEA 1.00% |

The bar compositions in Example 1 and 2 (with different amounts of stearate soap) were found to improve use up rate. The reduction of stearate soap, increases the bar use-up in Example 2 and Comparative 2 when compared to Example 1 and Comparative 1.

Examples 3–6

Stearyl Alcohol-Free Formulations

The following samples were prepared using the method in Example 1, but without the use of stearyl alcohol as a structurant. The only variations between the samples in TABLE C are the glycerin and DBS levels. Note, for the use-up data, two bars were used for each Example formulation evaluated. The use-up tests were done using the procedure described above.

TABLE C

| Example | wt % glycerin | wt % DBS | wt % Na stearate | wt % salt | % Use Up | Average % Use Up | Ttest - vs. 6 | Ttest - vs. 5 | Ttest - vs. 4 |
|---|---|---|---|---|---|---|---|---|---|
| 3 | 0.0 | 0.0 | 15.2 | 0 | 12.4 | 12.3 +/− 0.5 | 0.001 | 0.002 | 0.291 |
| | 0.0 | 0.0 | 15.2 | 0 | 12.3 | | | | |
| 4 | 4.0 | 0.0 | 15.2 | 0 | 12.0 | 11.3 +/− 0.5 | 0.019 | 0.087 | |
| | 4.0 | 0.0 | 15.2 | 0 | 10.5 | | | | |
| 5 | 0.0 | 0.5 | 15.2 | 0 | 9.0 | 8.9 +/− 0.5 | 0.008 | | |
| | 0.0 | 0.5 | 15.2 | 0 | 8.7 | | | | |
| 6 | 4.0 | 0.5 | 15.2 | 0 | 6.0 | 5.8 +/− 0.5 | | | |
| | 4.0 | 0.5 | 15.2 | 0 | 5.6 | | | | |

Example 6, which includes the combination of glycerin and DBS, has the lowest use up rate and is significantly different from all other samples, including the addition of DBS or glycerin alone. Statistical significance was defined using the Student T-Test, 2 tailed well known in the art. The p-values are displayed above. The composition of Example 6 was found to have a surprising effect that improved use up, even when a structurant, stearyl alcohol, is removed from the formula.

Examples 7–11

Formulations Including Sodium Chloride

Examples 7–11 as listed in TABLE D were prepared using the method described in Examples 3–6. In Examples 7–11 the sodium chloride level is at 1%.

TABLE D

| Example | Wt % glycerin | Wt % DBS | Wt % Na stearate | Wt % Salt | % Use Up | Average % Use Up | Ttest vs Ex. 11 |
|---|---|---|---|---|---|---|---|
| 7 | 0 | 0 | 15.2 | 0 | 12.4 | 12.3 +/− 0.5 | 0.042 |
| | 0 | 0 | 15.2 | 0 | 12.3 | | |
| 8 | 4 | 0 | 15.2 | 1 | 9.6 | 10.2 +/− 0.5 | 0.144 |
| | 4 | 0 | 15.2 | 1 | 10.7 | | |
| 9 | 0 | 0 | 15.2 | 1 | 9.8 | 9.7 +/− 0.5 | 0.165 |
| | 0 | 0 | 15.2 | 1 | 9.5 | | |
| 10 | 0 | 0.5 | 15.2 | 1 | 7.0 | 6.8 +/− 0.5 | 0.623 |
| | 0 | 0.5 | 15.2 | 1 | 6.6 | | |
| 11 | 4 | 0.5 | 15.2 | 1 | 6.4 | 7.4 +/− 0.5 | |
| | 4 | 0.5 | 15.2 | 1 | 8.5* | | |

*The two samples in Example 11 had different results for bar wear beyond the expected sample to sample variation. This unexpected result may have been due to operator error in washing time, water temperature fluctuations, or excess water in the soap dish during the testing.

In the test run using Examples 7, 8, 9, 10, and 11, the data showed an anomaly. Samples containing DBS and glycerin had an average use up rate that was higher than the other examples. The p-value for the Example 11 indicates that it is only significantly different from the negative control (no additives for use-up). This is likely due to the large variation in the results within Example 11.

Examples 12–17

Variation in Sodium Chloride and Sucrose

Another set of bars was prepared following the method of Example 1, but without stearyl alcohol and with variations in the sodium chloride and sucrose levels.

TABLE E

| Ex. # | wt/wt % glycerin | wt/wt % DBS | wt/wt % salt | wt/wt % Na stearate | wt/wt % sucrose | % Use Up | Average | T-Test vs. Example 17 |
|---|---|---|---|---|---|---|---|---|
| 12 | 0.0 | 0.0 | 0.0 | 15.2 | 0.0 | 24.7 | 25.8 +/ 0.5 | 0.0083 |
| | 0.0 | 0.0 | 0.0 | 15.2 | 0.0 | 26.8 | | |
| 13 | 4.0 | 0.0 | 0.0 | 15.2 | 0.0 | 24.0 | 23.9 +/− 0.5 | 0.0009 |
| | 4.0 | 0.0 | 0.0 | 15.2 | 0.0 | 23.7 | | |
| 14 | 4.0 | 0.0 | 1.0 | 15.2 | 4.0 | 20.0 | 19.7 +/− 0.5 | 0.0051 |
| | 4.0 | 0.0 | 1.0 | 15.2 | 4.0 | 19.4 | | |
| 15 | 0.0 | 0.5 | 0.0 | 15.2 | 4.0 | 18.9 | 18.8 +/− 0.5 | 0.0033 |
| | 0.0 | 0.5 | 0.0 | 15.2 | 4.0 | 18.7 | | |
| 16 | 0.0 | 0.5 | 1.0 | 15.2 | 0.0 | 18.0 | 17.7 +/− 0.5 | 0.0129 |
| | 0.0 | 0.5 | 1.0 | 15.2 | 0.0 | 17.5 | | |
| 17 | 4.0 | 0.5 | 1.0 | 15.2 | 4.0 | 14.3 | 14.5 +/− 0.5 | |
| | 4.0 | 0.5 | 1.0 | 15.2 | 4.0 | 14.7 | | |

In the Example 17 above, the combination of DBS and glycerin improved use up rate, and was significantly different from the other formulations without this combination and with varying levels of sucrose and sodium chloride. This test was performed separately and variations from the previous tests are believed to have resulted from environmental conditions and operator variability.

Example 18

Definition of Clarity and Evaluation of Bar Clarity

For Example 18, a bar was made using the procedure described for Example 1. The clarity of bars from Examples 1, 2 and 18 were evaluated using percent transmittance by placing a 1 cm thick sample of the bar in the beam of a spectrophotometer whose range includes the visible spectrum, such as a Shimadzu UV 160 U Spectrophometer. Within the context of this invention, a bar is deemed to be transparent (clear) if the maximum transmittance of light of any wavelength in the range 400–800 nm through a 1 cm sample is at least 35%, preferably at least 50%. The bar is deemed translucent if the maximum transmittance of such light through the sample is between 2% and less than 35%. A bar is deemed opaque if the maximum transmittance of such a light is less than 2%. This definition is based on European Patent Application Publication Number 291,334 A2. Thus, there are differences between transparent (clear), translucent, and opaque compositions. In an alternative view, a definition of clear or transparent composition allows for ready viewing of an object behind it. A translucent composition, although light passes through, scatters light in such a manner that it is impossible to clearly identify objects behind the translucent bar. Opaque bars do not permit light to pass through. An alternative definition that is standard to the trade for translucent is the visual perception of transmittance of any light through a ¼ inch thick portion of the bar. Transparency may be defined as the ability to read 14 point type though a quarter inch thick section of the bar. For purposes of this invention, the quantitative definition of light transmittance will be used.

Samples made according to Example 1 were tested with the method described above. Each sample was evaluated with a minimum of two readings. The average results are shown below in TABLE E. Note that the clarity of bars, with compositions of the invention, were found to have a maximum transmittance at 800 nm.

TABLE E

| Ingredient (wt %) | Example 1 (wt %) | Example 2 (wt %) | Example 18 (wt %) |
|---|---|---|---|
| Propylene Glycol | 16.00 | 16.00 | 16.00 |
| Dipropylene Glycol | 2.00 | 2.00 | 2.00 |
| Glycerin | 4.00 | 4.00 | 4.00 |
| Dibenzylidene sorbitol | 0.25 | 0.25 | 0.25 |
| Cocoamidopropyl Betaine (30% active) | 8.73 | 8.73 | 8.73 |
| Sodium Chloride | 1.00 | 1.00 | 1.00 |
| Stearic Acid | 12.00 | 9.23 | 12.00 |
| Myristic Acid | 7.30 | 7.30 | 7.30 |
| Coconut Acid | 3.50 | 3.50 | 3.50 |
| Sodium Hydroxide (50% active) | 6.77 | 5.86 | 6.77 |
| Ethanol | 0.20 | 0.20 | 0.20 |
| Sucrose | 4.00 | 4.00 | 4.00 |
| Sodium Laureth Sulfate (70% active) | 12.00 | 12.00 | 12.00 |
| Cocamide MEA | 2.00 | 2.00 | 2.00 |
| Disodium Lauryl Sulfosuccinate | 4.50 | 4.50 | 4.50 |
| Sodium Lauryl Sulfate | 4.00 | 4.00 | 4.00 |
| Stearyl Alcohol | 3.00 | — | — |
| Fragrance | 1.00 | 1.00 | 1.00 |
| Water | 5.2499 | 11.9299 | 8.2499 |
| Soybean Oil | 2.50 | 2.50 | 2.50 |
| Colorant | 0.0001 | 0.0001 | 0.0001 |
| Total | 100 | 100 | 100 |

TABLE F

| EXAMPLE | Average % Transmittance at 800 nm |
|---|---|
| 2 | 17.2% |
| 18 | 10.5% |
| 1 | 2.6% |

The bars from Examples 1, 2 and 18 were deemed to be translucent. Transparency can be increased, however, by pouring the formulations at a low fill temperature for example in the range of 55–60 degrees, particularly about 57 degrees C.

What is claimed is:

1. A is a non-transparent cleansing bar comprising:

(a) from about 3 to about 40 weight % anionic soap;

(b) from about 4 to about 40 weight % of at least one synthetic surfactant;

(c) from 0.1 to about 10 weight % of a primary gelling agent from the group consisting of dibenzylidene sorbitol, dibenzylidene xylitol, dibenzylidene ribitol, and mixtures thereof;

(d) from about 5 to about 60 weight % of a humectant, provided that glycerin is a component of the humectant and is present in an amount of about 2 to about 10 weight %; and (e) water;

wherein all amounts are in % by weight based on the weight of the entire composition.

2. A cleansing bar according to claim 1 comprising from 14–45 weight % water.

3. A cleansing bar according to claim 1 or claim 2 comprising from 17–35 weight % water.

4. A cleansing bar according to claim 1 additionally comprising one or more members selected from the group consisting of:

(f) from 0 to about 5 wt. % of one or more secondary structurants selected from the group consisting of (i) cellulose and guar derivatives; (ii) acrylic acid polymers; (iii) polyacrylamides; (iv) alkylene/alkylene oxide polymers; (v) clays; (vi) hydrated and fumed silicas; (vii) gelatin; (ix) xanthan and guar gums; (x) carrageenan; (xi) agar; and (xii) alginates; and (g) 0.2–3 weight % of a monohydric alcohol such as 0.1–2 weight % of an alcohol selected from the group consisting of methanol, ethanol, propanol and isopropanol.

5. A cleansing bar according to claim 1 wherein the anionic soap comprises a C12–18 alkyl, optionally with some unsaturation, and with up to 20% of bonds as a carboxylic acid salt having cations selected from the group consisting of sodium, potassium, ammonium and hydroxyethyl ammonium.

6. A cleansing bar according to claim 1 wherein the anionic soap comprises a minimum of about 5–10 weight % of the bar.

7. A cleansing bar according to claim 1 wherein the anionic soap comprises a maximum of about 25–30 weight % of the composition.

8. A cleansing bar according to claim 1 wherein the synthetic surfactant is selected from the group consisting of at least one of an anionic, amphoteric, zwitterionic, nonionic and cationic surfactants, and mixtures of any of the foregoing.

9. A cleansing bar according to claim 1 comprising an anionic surfactant selected from the group consisting of alkyl sulfates, anionic acyl sarcosinates, methyl acyl taurates, N-acyl glutamates, acyl isethionates, alkyl ether sulfates, alkyl sulfosuccinates, alkyl phosphate esters, ethoxylated alkyl phosphate esters, trideceth sulfates, protein condensates, mixtures of ethoxylated alkyl sulfates and mixtures of any of the foregoing having C8–22 alkyl chains.

10. A cleansing bar according to claim 1 wherein the anionic surfactant is selected from the group consisting of:

(a) sodium, ammonium, potassium and triethanolamine alkyl sulfates having 8–18 carbons;

(b) sodium coconut oil fatty acid monoglyceride sulfates and sulfonates;

(c) sodium and potassium salts of sulfuric acid esters of the reaction product of 1 mole of a higher fatty alcohol and 1 to 12 moles of ethylene oxide;

(d) sodium and potassium salts of alkyl phenol ethylene oxide ether sulfate with 1 to 10 units of ethylene oxide per molecule and in which the alkyl radicals contain from 8 to 12 carbon atoms;

(e) sodium alkyl glyceryl ether sulfonates;

(f) reaction products of fatty acids having from 10 to 22 carbon atoms esterified with isethionic acid and neutralized with sodium hydroxide;

(g) water soluble salts of condensation products of fatty acids with sarcosine; and (h) mixtures of any of the foregoing.

11. A cleansing bar according to claim 8 comprising a zwitterionic surfactant selected from the group consisting of derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group selected from the group consisting of carboxy, sulfonate, sulfate, phosphate, and phosphonate.

12. A cleansing bar according to claim 8 comprising a zwitterionic surfactant selected from the group consisting of compounds of the following formula:

$$\begin{array}{l}\qquad\; (R^3)_x \\ \qquad\quad | \\ R^2 - Y^{(+)} - CH_2 - R^4 - Z^{(-)}\end{array}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

13. A cleansing bar according to claim 8 comprising a zwitterionic surfactant selected from the group consisting of: 4-[N,N-di(2-hydroxyethyl)-N-octadecylammonio]-but-ane-1-carboxylate; 5-[S-3-hydroxypropyl-S-hexadecylsulfonio]-3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio)propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl)ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; 5-[N,N-di(3-hydroxypropyl)-N-hexadecylammonio]-2-hydroxy-pentane-1-sulfate; and mixtures of the foregoing.

14. A cleansing bar according to claim 8 comprising an amphoteric surfactant selected from the group consisting of derivatives of aliphatic secondary and tertiary amines in which the aliphatic radical can be straight chain or branched and wherein one of the aliphatic substituents contains from about 8 to about 18 carbon atoms and one contains an anionic water solubilizing group selected from the group consisting of carboxy, sulfonate, sulfate, phosphate, and phosphonate.

15. A cleansing bar according to claim 8 comprising an amphoteric surfactant selected from the group consisting of sodium 3-dodecylaminopropionate, sodium 3-dodecylaminopropane sulfonate; N-alkyltaurines; N-higher alkyl aspartic acids; and mixtures of the forgoing.

16. A cleansing bar according to claim 8 comprising an amphoteric surfactant selected from the group consisting of cocodimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, lauryl bis-(2-hydro-xypropyl)alpha-carboxyethyl betaine, cocodimethyl sulfopropyl betaine, stearyl dimethyl sulfopropyl betaine, amido betaines, amidosulfobetaines, and mixtures of the foregoing.

17. A cleansing bar according to claim 8 comprising a cationic surfactant selected from the group consisting of:

stearyldimenthylbenzyl ammonium chloride; dodecyltrimethylammonium chloride;

nonylbenzylethyldimethyl ammonium nitrate; tetradecylpyridinium bromide;

laurylpyridinium chloride; cetylpyridinium chloride; laurylpyridinium chloride;

laurylisoquinolium bromide; ditallow(hydrogenated)dimethyl ammonium chloride; dilauryldimethyl ammonium chloride; stearalkonium chloride; and mixtures of the foregoing.

18. A cleansing bar according to claim 8 comprising a nonionic surfactant selected from the group consisting of:

(a) polyethylene oxide condensates of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol, and wherein the alkyl substituent is derived from polymerized propylene, diisobutylene, octane, or nonane;

(b) products formed from condensation of ethylene oxide with a product resulting from reaction of propylene oxide and ethylene diamine products and selected from the group consisting of compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000;

(c) condensation products of aliphatic alcohols having from 8 to 18 carbon atoms, in either straight chain or branched chain configuration with ethylene oxide;

(d) ethoxylated fatty acid esters of polyhydric alcohols;

(e) long chain tertiary amine oxides corresponding to the following formula:

$$(R^{11})(R^{12})(R^{13})N\rightarrow O$$

wherein $R^{11}$ contains an alkyl, alkenyl or monohydroxy alkyl radical of from about 8 to about 18 carbon atoms, from 0 to about 10 ethylene oxide moieties, and from 0 to 1 glyceryl moiety, and, $R^{12}$ and $R^{13}$ may be the same or different and each contain from 1 to about 3 carbon atoms and from 0 to about 1 hydroxy group selected from the group consisting of methyl, ethyl, propyl, hydroxy ethyl, and hydroxy propyl radicals;

(f) long chain tertiary phosphine oxides corresponding to the following formula:

$$(R^{21})(R^{22})(R^{23})P\rightarrow O$$

wherein $R^{21}$ contains an alkyl, alkenyl or monohydroxyalkyl radical ranging from 8 to 20 carbon atoms in chain length, from 0 to about 10 ethylene oxide moieties and from 0 to 1 glyceryl moiety and $R^{22}$ and $R^{23}$ are each alkyl or monohydroxyalkyl groups containing from 1 to 3 carbons;

(g) long chain dialkyl sulfoxides containing one short chain alkyl or hydroxy alkyl radical of 1 to about 3 carbon atoms and one long hydrophobic chain which contains alkyl, alkenyl, hydroxy alkyl, or keto alkyl radicals containing from about 8 to about 20 carbon atoms, from 0 to about 10 ethylene oxide moieties and from 0 to 1 glyceryl moiety;

(h) alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0; and (i) mixtures of any of the foregoing.

19. A cleansing bar according to claim 1 wherein the humectant is selected from the group consisting of propylene glycol, dipropylene glycol, glycerin, sorbitol, mannitol, xylitol, hexylene glycol, and mixtures of any of the foregoing.

20. A cleansing bar according to claim 1 comprising a minimum of about 8 weight % humectant.

21. A cleansing bar according to claim 1 comprising a maximum of about 50 weight % humectant.

22. A cleansing bar according to claim 1 additionally comprising 0.1–2 weight % of a lower monohydric alcohol selected from the group consisting of methanol, ethanol, propanol, isopropanol, and mixtures thereof.

23. A cleansing bar according to claim 1 comprising a minimum of 0.1–0.5 weight % of the primary gellant.

24. A cleansing bar according to claim 1 comprising a maximum of 1–2 weight % of the primary gellant.

25. A cleansing bar according to claim 1 comprising 0.2%–1.0% dibenzylidene sorbitol as the primary gallant.

26. A cleansing bar according to any one of claims 1, 2, and 23–25 additionally comprising a secondary structurant.

27. A cleansing bar according to any one of claims 1, 2, and 23–25 additionally comprising a secondary structurant selected from the group consisting of alkali halides and alkali metal sulfates.

28. A cleansing bar according to any one of claims 1, 2, and 23–25 additionally comprising at least about 1% of sodium chloride as a secondary structurant.

29. A cleansing bar according to any one of claims 1, 2 and 23–25 which is alcohol-free.

30. A cleansing bar according to claim 1 comprising:
(a) from about 3 to about 40 weight % soap; (b) from about 4 to about 40 weight % of at least one synthetic surfactant; (c) from about 14 to about 45 weight % water; (d) from 0.1 to about 10 weight % of a gelling agent from the group consisting of dibenzylidene sorbitol, dibenzylidene xylitol, dibenzylidene ribitol, and mixtures thereof; (e) from 0.2 weight % to about 3 weight % lower monohydric alcohol having 1–3 carbons; and (f) from about 5 to about 60 weight % of a humectant provided that glycerin is a component of the humectant and is present in an amount of about 2 to about 10 weight %; wherein all amounts are in % by weight based on the weight of the entire composition.

31. A cleansing bar according to claim 1 additionally comprising in an amount of up to 5 weight % at least one ingredient selected from the group consisting of one or more secondary structurants selected from the group consisting of hydroxypropyl cellulose; smectite hydrophilic and/or organo clays; and hydrated and fumed silicas.

* * * * *